US011730566B2

(12) United States Patent
Fontein et al.

(10) Patent No.: US 11,730,566 B2
(45) Date of Patent: Aug. 22, 2023

(54) DEVICE FOR STORAGE AND APPLICATION AND METHOD

(71) Applicant: VOCO GMBH, Cuxhaven (DE)

(72) Inventors: Nils Fontein, Cuxhaven (DE); Manfred Thomas Plaumann, Cuxhaven (DE); Uwe Leiner, Cuxhaven (DE)

(73) Assignee: VOCO GMBH, Cuxhaven (DE)

( * ) Notice: Subject to any disclaimer, the term of this patent is extended or adjusted under 35 U.S.C. 154(b) by 0 days.

(21) Appl. No.: 16/645,297

(22) PCT Filed: Jul. 26, 2019

(86) PCT No.: PCT/EP2019/070215
§ 371 (c)(1),
(2) Date: Mar. 6, 2020

(87) PCT Pub. No.: WO2020/025485
PCT Pub. Date: Feb. 6, 2020

(65) Prior Publication Data
US 2021/0137639 A1 May 13, 2021

(30) Foreign Application Priority Data
Jul. 31, 2018 (DE) ............... 10 2018 118 577.4

(51) Int. Cl.
*A61C 5/62* (2017.01)
*A61C 5/66* (2017.01)
(Continued)

(52) U.S. Cl.
CPC .............. *A61C 5/62* (2017.02); *A61C 5/66* (2017.02); *A61C 19/003* (2013.01); *A61K 6/20* (2020.01); *A61K 6/831* (2020.01)

(58) Field of Classification Search
CPC ........ B05C 17/00516; B05C 17/00593; B65D 83/0005–005; A61C 5/60; A61C 5/62; A61C 5/64; A61C 5/66; A61C 9/0026
See application file for complete search history.

(56) References Cited

U.S. PATENT DOCUMENTS 5,122,057 A 6/1992 Discko, Jr.
5,190,800 A * 3/1993 Yamada .................. G11B 7/253
430/270.16
(Continued)

FOREIGN PATENT DOCUMENTS

DE 10218859 11/2003
DE 102013004077 9/2014
(Continued)

*Primary Examiner* — Amy R Sipp
*Assistant Examiner* — Sydney J Pulvidente
(74) *Attorney, Agent, or Firm* — Duane Morris L.L.P; Gregory M. Lefkowitz; Brandon A. Chan

(57) ABSTRACT

The present invention relates in particular to the storage of dental material in a device (10, 10') and the application of the dental material (20) from such a device (10,10'), and a method for treating dental material (20). In order to provide a solution that allows the simple and practical handling of a dental material (20) in the sense of storage, application and/or treatment thereof, inter alia, a device (10, 10') for storage and application (20) comprising a cavity (12) for storage of the dental material (20) and a wall (14) surrounding the cavity (12) is proposed, wherein the wall (14) in at least a first temperature range is impermeable to radiation of at least a first wavelength or a first wavelength range in the range of 100 nm to 500 nm, wherein the wall (14) comprises at least one area that at least in a second temperature range is permeable to radiation of at least a second wavelength or a second wavelength range in the range of 600 nm to 50,000 nm.

16 Claims, 4 Drawing Sheets

Figure 1:
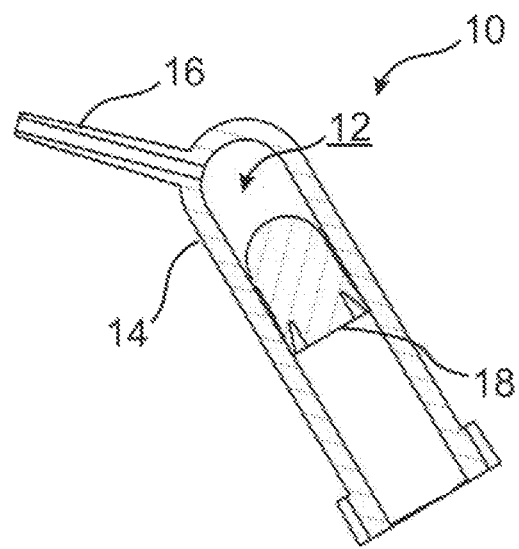

(51) Int. Cl.
*A61K 6/20* (2020.01)
*A61K 6/831* (2020.01)
*A61C 13/15* (2006.01)

(56) References Cited

U.S. PATENT DOCUMENTS

| | | |
|---|---|---|
| 6,312,254 B1 | 11/2001 | Friedman |
| 6,877,983 B1 | 4/2005 | Dragan et al. |
| 7,086,861 B2 | 8/2006 | Pitz et al. |
| 7,097,452 B2 | 8/2006 | Friedman |
| 8,376,573 B2 * | 2/2013 | Mehlmann ............ H01J 61/52 |
| | | 362/373 |
| 2004/0152041 A1 | 8/2004 | Metzbower |
| 2006/0204924 A1 | 9/2006 | Galehr et al. |
| 2012/0022541 A1 * | 1/2012 | McKay ............ A61B 17/8805 |
| | | 606/94 |
| 2014/0131393 A1 | 5/2014 | Sirkis |
| 2014/0212836 A1 * | 7/2014 | Fritze ................... A61C 5/62 |
| | | 433/90 |
| 2014/0248578 A1 | 9/2014 | Fritze et al. |
| 2015/0297325 A1 | 10/2015 | Boehm et al. |
| 2017/0119498 A1 * | 5/2017 | Discko .................. A61C 5/62 |
| 2018/0214247 A1 * | 8/2018 | Sharma ................. A61C 5/50 |
| 2019/0192386 A1 * | 6/2019 | Fukudome ............. A61K 6/17 |

FOREIGN PATENT DOCUMENTS

| | | | |
|---|---|---|---|
| DE | 102016106019 | 2/2017 | |
| EP | 0669113 | 8/1995 | |
| EP | 0848935 | 6/1998 | |
| EP | 2412448 | 2/2012 | |
| WO | 2005087129 | 9/2005 | |
| WO | 2009106352 | 9/2009 | |
| WO | WO-2012170230 A1 * | 12/2012 | ............ C09D 5/00 |
| WO | 2016014605 | 1/2016 | |

* cited by examiner

DEVICE FOR STORAGE AND APPLICATION AND METHOD

CROSS-REFERENCE TO RELATED APPLICATIONS

This application is a § 371 national stage entry of International Application No. PCT/EP2019/070215, filed on Jul. 26, 2019, which claims priority to German Patent Application No. 10 2018 118 577.4, filed on Jul. 31, 2018, the entire contents of which are incorporated herein by reference.

The present invention relates to the field of application of materials, and in particular the storage of dental material in a device and the application of the dental material from such a device, and a method for treating dental material.

A so-called compule can be considered to be an example of a device for storage and application of a dental material.

Compules are sufficiently well-known from the prior art as packing means for dental compounds (EP 1689314 A1, EP 2364123 A1, EP 2696794 A1, EP 0848935 A1, EP 2412448 A2, EP 0669113 B1, DE 10218859 A1, DE 102013004 077 A1, U.S. Pat. No. 6,877,983 B1). They make it possible to store a pre-proportioned amount of filling material for each patient so that a new, fresh material is used for each individual patient in every case and cross-contamination can be effectively excluded. In this manner, they allow a hygienic working procedure to be followed.

In order to liquefy dental materials so as to make them easier to dispense and to allow improved flow properties in the cavity, various solutions have been proposed for heating these materials.

U.S. Pat. No. 7,097,452 B2 describes a compule for the storage and heating of dental composites having a body composed of an electrically conductive and a thermally conductive plastic. An external power source is required for heating.

EP 1 740 119 A1 describes a compule for storing and dispensing dental composites having a body containing an energy output device. This energy output device is e.g. a heating wire arranged in a spiral shape for heating of the compule and the contents thereof.

U.S. Pat. No. 7,086,861 B2 discloses a compule for storing and dispensing dental composites having a body comprising an electrically operated induction coil used to heat the compule and thus the contents thereof.

In addition to these special heatable compules, the dispensers can also be configured to allow heating of the compules and the contents thereof.

EP 1190681 A2 discloses a dispenser that comprises an electrical heating unit and can thus heat standard compules together with the contents thereof.

DE 10 2016106019 A1 discloses a dispensing device for dental materials that comprises a layered heating body as a heating unit that heats the compule and the contents thereof.

WO 2016/014605 A1 discloses a self-heating sleeve that can either pre-heat a compule or is configured so that it can heat the compule in the dispenser.

It has been found that known approaches for heating dental materials have a variety of drawbacks. Particularly in cases where the compule or another type of device is first heated and then transfers heat to the dental material to be heated, there is a problem in heat transmission through the compule or device and in heat transfer from the compule or device to the dental material, wherein a thermal gradient is additionally generated in the dental material, making it impossible to achieve a desired increase in the flowability of the dental material in a uniform manner. In addition, it can happen during a slow heating process that the temperature of the compule material or of dental materials present in the vicinity of the wall becomes too high, at least unless corresponding countermeasures such as limiting the heating temperature are carried out, which in turn adversely affects the heat input.

An object of the present invention is to provide a device for storage and application of a dental material and a method for the treatment of a dental material that prevent the drawbacks of the prior art or only have such drawbacks to a minor extent.

It is therefore desired to present a solution that allows the simple and practical handling of a dental material in the sense of storage, application and/or treatment thereof.

According to a first aspect of the invention, a device for storage and application is proposed, as defined in claim 1, specifically comprising a cavity for storage of the dental material and a wall surrounding the cavity, wherein the wall, in at least a first temperature range, is impermeable to radiation of at least a first wavelength or a first wavelength range in the range of 100 nm to 500 nm, and wherein the wall, A) has at least one area that at least in a second temperature range is permeable to radiation of at least a second wavelength or a second wavelength range in the range of 600 nm to 50,000 nm and/or B) has at least one area with a carrier material, preferably a polyamide material and/or a polybutylene terephthalate material and a filter material which is provided externally on the carrier material, internally on the carrier material and/or between at least two layers of the carrier material and/or is embedded in the carrier material, wherein the filter material is selected from the group composed of perylene derivatives

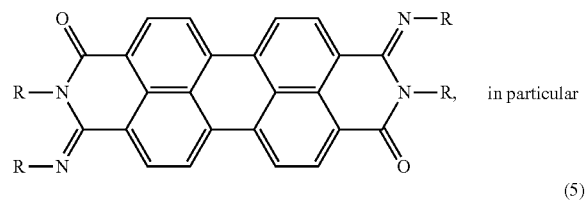

and combinations thereof.

According to a second aspect of the invention, a method is proposed for treating a dental material, in particular outside the human or animal body, as defined in claim 16, specifically comprising the steps of providing a device according to the invention comprising radiation-curable dental material in the first temperature range, and irradiating the provided device with radiation of the second wavelength or the second wavelength range, preferably with IR light of a wavelength in the range of 600 nm to 50,000 nm, in order to heat the dental material and reduce the viscosity of the dental material by means of heating to a desired viscosity or less.

Part of the background of the present invention can be found in the following considerations.

Light-curing or general radiation-curable dental materials, i.e. dental materials that are irradiated in order to initiate a curing process and/or support said process with light of a specified wavelength or a specified wavelength range, must be protected against this radiation prior to use. For other dental materials as well, it may be important to prevent or at least largely reduce undesired incidence of light. A typical approach for preventing the incidence of light lies in mixing the material of the packaging (for example, the compule material) with lamp black (carbon black) so that a light-impermeable material is produced.

There is particular sensitivity in the present sense for light of a wavelength in the range of 100 to 500 nm.

As direct irradiation, for example of a compule with infrared radiation, is provided instead of direct heat transfer from a heater to the compule material or heat transfer from the heater to the air and then to the compule material, although this leads to heating of the compule material, which for example is mixed with carbon black, the infrared radiation does not reach the dental material itself, as the infrared radiation is absorbed by the compule material or the lamp black/carbon black contained therein.

It has now been realised that it is possible in a device for the storage and application of a dental material to combine protection of the dental material against undesired passage of light with permeability to infrared radiation, so that undesired radiation is blocked, but the heating infrared radiation can reach directly onto or into the dental material.

Although the entire range of infrared radiation can basically be used within the context of the invention, there is a particular preference for radiation in the near infrared region (750 to 3,000 nm wavelength).

It should be borne in mind in implementing the invention that the wall area provided for penetration of the radiation at least of the second wavelength or the second wavelength range, due to the material of the wall, may have one or a plurality of absorption areas for one or a plurality of wavelengths between 600 and 50,000 nm, wherein it is then to be understood that the radiation used for heating the dental material should not be present only in such an absorption area. For example, if an infrared LED with a relatively narrow emission band is provided for heating the dental material, the LED and the wall are to be selected such that emission and absorption do not substantially coincide.

Even if a significant proportion of the areas of application of a method according to the above second aspect, because of the nature and purpose of the dental material, provides for method steps on or in the human or animal body, methods according to the invention that do not comprise therapeutic aspects per se are also to be taken into consideration. In this context, one can mention for example the use of the dental material for non-therapeutic methods (e.g. as a filling material, an underfilling material, a luting material or a repair or sealing agent for materials (such as stone), which in the broadest sense are comparable with a dental material) or use for testing or training purposes.

In the context of the present invention, the term "impermeable" is not to be understood as limited solely to complete impermeability in the sense of 100% absorption and/or reflection, wherein "impermeable" comprises transmittance of less than 10%, preferably less than 5%, and particularly preferably less than 1%. To the extent technically feasible, however, impermeability that is complete from a practical standpoint can also be provided.

Similarly, the term "permeable" refers not only to complete transmission without scattering, reflection and/or absorption, wherein transmittance of more than 50%, preferably more than 65%, and particularly preferably more than 80% is to be considered "permeable". Unless otherwise dictated by circumstances, it should be clear that permeability that is complete from a practical standpoint is generally particularly advantageous. Provided that the initial energy input (i.e. the irradiated light quantity) as such is not subject to special restrictions, reflection and scattering as such can also be completely excluded when considering the term "permeable", so that in this sense a permeability is given if the transmittance is merely greater than the absorbance, whereby here a minimum ratio of transmittance to absorbance of 3:1, particularly of 5:1, especially of 10:1 is preferred.

It has been found that with the above-mentioned combination of a carrier material (in particular polyamide) and a filter material in the form of one or more perylene derivatives, advantageous results can be achieved regardless of whether the transmittance (including scattering, reflection and/or absorption) is greater than 50%. Since this combination may well also fulfil the features of aspect A), there is a certain overlap between aspects A) and B), whereas aspect B) also concerns devices (not covered as such by aspect A)) in which the wall has only one area with the given combination of carrier material and filter material, but without being "permeable" in the sense of a transmittance (including scattering, reflection and/or absorption) of more than 50%. It should be clear that the area with the carrier material and the filter material can also extend over the entire wall of the device. With regard to the relative amount of the filter material to the carrier material, a proportion of 0.1 to 8 wt % is preferred, in particular 0.2 to 5 wt %, especially preferably 0.5 to 2 wt %.

In an advantageous embodiment of an aspect of the invention, the area of the wall comprises or is composed of a filter material, wherein the filter material at least in the first temperature range, preferably at least in the first temperature range and in the second temperature range, has a transmittance with respect to radiation of the first wavelength or the first wavelength range of less than 10%, preferably less than 5%, wherein the filter material, at least in the second temperature range, has a transmittance with respect to radiation of the second wavelength or the second wavelength range of more than 50%, preferably more than 65%, and particularly preferably more than 80%.

The use of a filter material with a low transmittance with respect to the first wavelength or the first wavelength range, at least in the first temperature range, makes it possible to effectively protect the dental material against undesired irradiation. Here, it is not absolutely necessary, although it is preferable, for the filter material also to have such low transmittance at least in the second temperature range (particularly preferably also in the range between the first and the second temperature range). If the filter material partially or completely loses its filtering action with increasing temperature, an effect of the radiation can nevertheless be prevented or at least reduced with correspondingly rapid application.

If the filter material already has high permeability to the radiation used to heat the dental material of the second wavelength or the second wavelength range in the area of the first and the second temperature ranges and optionally in between, this radiation can directly reach onto or into the dental material in order to heat it. It would not be harmful if the filter material for example had a higher absorbance in the first temperature range, provided that the absorption of heat connected with said absorbance provides a desired permeability, at least in the second temperature range.

Preferably, the filter material shows no or at least essentially no temperature dependency with respect to its permeability to the radiation of the respective wavelengths or wavelength ranges, wherein a filter material with a significant temperature dependency, e.g. a linear temperature dependency in contrast to a temperature dependency of a thermochromic material, is not excluded from the scope of the invention, provided that the above-mentioned conditions are met.

In a preferred variant of the above embodiment, the filter material is selected from the group composed of substances with a perylene skeleton, aromatic diazo compounds and combinations thereof.

In the context of the invention, substances with a perylene skeleton (Formula 1) have been recognized to be suitable as IR-transparent colour pigments.

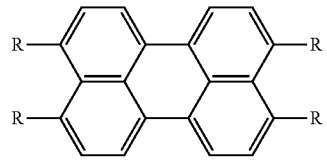
(1)

For example, the perylene tetracarboxylic acid derivatives of formula 2 can be used.

Here, X denotes O, NH or NR, wherein R can be an alkyl group, a hydroxyalkyl group, an aromatic or a substituted aromatic group. N,N'-bis(2-phenylethyl)perylene-3,4:9,10-bis(dicarboximide) (X=NCH$_2$CH$_2$Ph) is for example commercially available under the brand names Paliogen® Black S 0084 or C.I. Pigment Black 31. N,N'-bis(4-methoxybenzyl)perylene-3,4:9,10-bis(dicarboximide) (X=NCH$_2$(C$_6$H$_4$)OCH$_3$) is for example commercially available under the brand names Paliogen® Black L 0086 or C.I. Pigment Black 32.

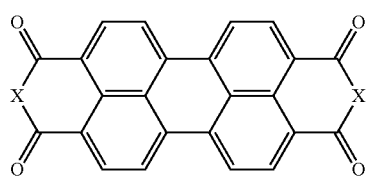
(2)

Also found to be particularly suitable were the perylene derivatives (3) or (4), in particular if the N—R groups form imidazoles or pyrimidones, and annulated imidazoles or pyrimidones. Particularly preferred are the corresponding perylene derivatives (5) and (6). Such colour pigments are commercially available as Lumogen® Black K0087 and Lumogen® Black K0088.

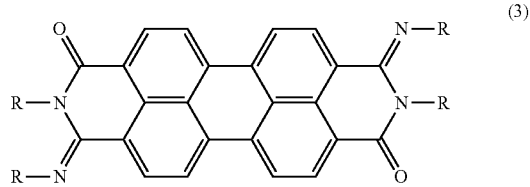
(3)

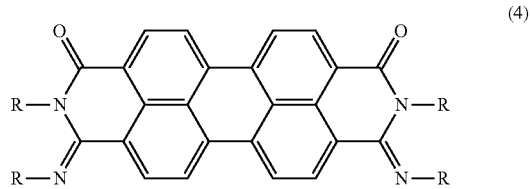
(4)

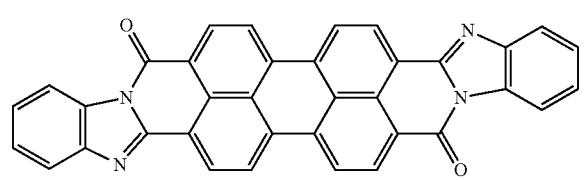
(5)

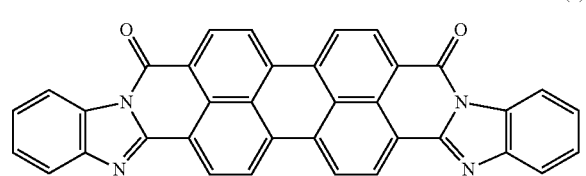
(6)

Further IR-transparent colour pigments suitable for the invention include aromatic diazo compounds of General Formula 7.

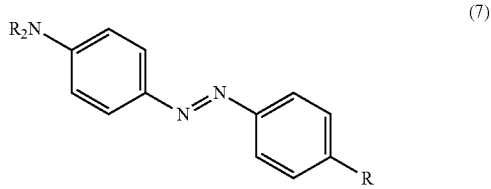
(7)

Examples are 4-(dimethylamino)-4'-aminoazobenzene or diazo black (8) or azomethine black (9).

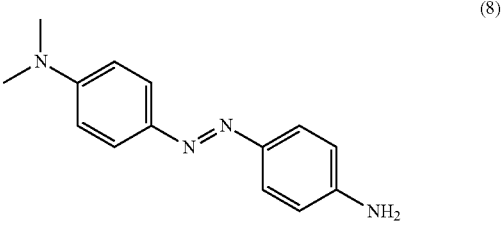
(8)

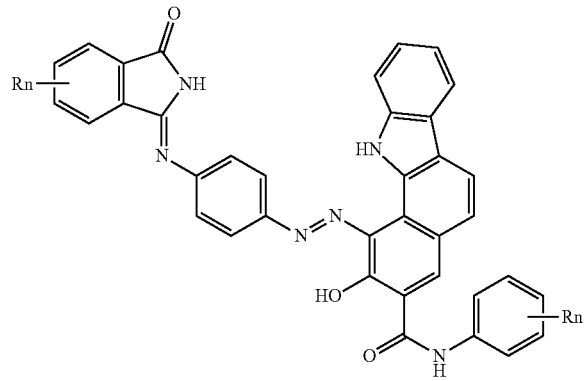

(9)

The dyes mentioned here can be used as such or in microencapsulated form. Advantageously, these dyes or microencapsulated dyes are first used to produce a master batch or coloured granules, which are then added to the plastic to be dyed.

In another advantageous embodiment of an aspect of the invention, which is provided as an alternative or supplement to the above embodiment, the area of the wall comprises or is composed of thermochromic material that has a switching temperature in the range of 25 to 50° C., wherein the thermochromic material, at a temperature below the switching temperature, has a lower transmittance with respect to radiation at least of the second wavelength or the second wavelength range than at a temperature above the switching to temperature.

The thermochromic material having a lower transmittance in the lower temperature range with respect to the radiation of the second wavelength or the second wavelength range is first heated by the radiation so that because of this increase in temperature, the switching temperature of the thermochromic material is finally reached or exceeded, so that the thermochromic material becomes (more) permeable to the radiation.

In this case as well, if the exposure is sufficiently brief (or if an environment is avoided in which radiation of the first wavelength or the first wavelength range is present), it is not harmful if switching over of the thermochromic material also results in higher permeability to this radiation.

In a preferred variant of the above embodiment, the thermochromic material is selected from the group composed of inorganic pigments comprising metal salts or metal oxides in which a colour transition takes place due to a phase transmission, a change in the ligand geometry, a change in the coordination number and/or a change in the crystal field, organic pigments comprising thermochromic liquid crystals, conjugated polymers and leuco dyes and combinations thereof.

Inorganic or organic pigments can be used as an example of a thermochromic material that can be used in the context of the present invention.

Inorganic pigments are metal salts or metal oxides in which a colour transition takes place due to phase transitions, a change in the ligand geometry, a change in coordination number or a change in the crystal field.

Organic pigments include thermochromic liquid crystals, conjugated polymers and leuco dyes. Examples of thermochromic liquid crystals include cholesterol derivatives or cyanobiphenyls. Conjugated polymers can show changes in colour due to conformation changes. Systems based on spiropyrans (Formula 11), spirooxazines (Formula 12), salicylic Schiff bases (Formula 13), bianthrones (Formula 14), indolyl phthalides (Formula 15) or fluoranes (Formula 16) can be used as leuco dyes.

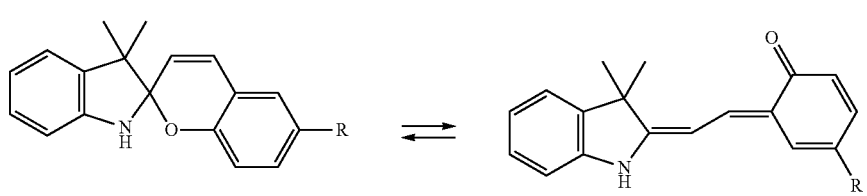

(11)

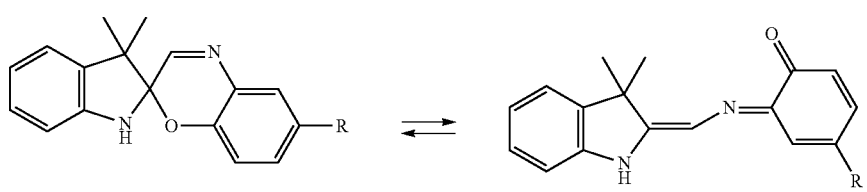

(12)

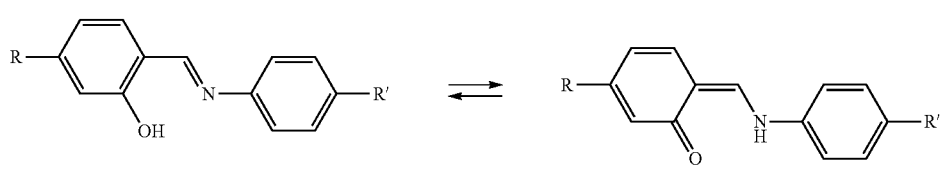

(13)

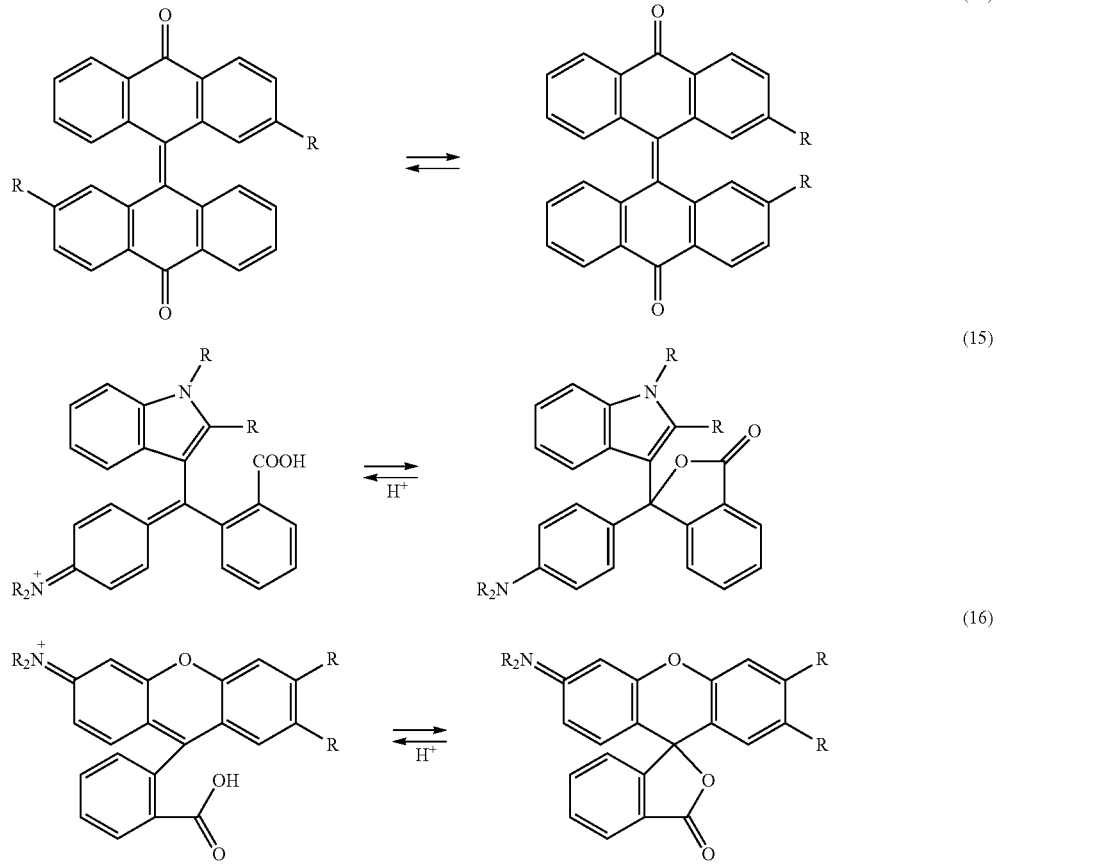

Such systems are composed as a rule of an electron donor (spiropyrans, spirooxazines, salicylic Schiff bases, bianthrones, indolyl phthalides or fluoranes) and an electron acceptor. Various colours can be set using the electron donors by suitable selection of the substituents. In addition to the positions for the substituents shown in simplified form in the formulae, other positions are also conceivable. Phenols, azoles or organic acids are used as electron acceptors. Examples of phenols are phenyl phenol, bisphenol A, bisphenol AP, bisphenol AF, bisphenol FL, cresol, resorcinol, chlorlucinol, phenol, phenol oligomers, naphthol, 1,5-dihydroxynaphthaline, pyrocatechol and pyrogallol. Examples of azoles are benzotriazoles such as 5-chlorbenzotriazole, 4-laurylaminosulfobenzotriazole, 5-butylbenzotriazole, dibenzotriazole, 2-Oxybenzotriazole, 5-ethoxycarbonylbenzotriazole, 5,5'-methylene bisbenzotriazole, imidazoles such as oxybenzimidazole, and tetrazoles. Examples of organic acids include aromatic and aliphatic carboxylic acids and substituted derivatives thereof. Examples of aromatic carboxylic acids are salicylic acid, methylene bissalicylic acid, resorcylic acid, gallic acid, benzoic acid, p-oxybenzoic acid, pyromellitic acid, naphthoic acid, tannic acid, toluic acid, trimellitic acid, phthalic acid, terephthalic acid and anthranilic acid. Examples of aliphatic carboxylic acids are acids with 1 to 20 carbon atoms, preferably 3 to 15 carbon atoms, such as e.g. stearic acid, 1,2-hydroxystearic acid, tartaric acid, citric acid, oxalic acid and lauric acid.

The thermochromic material or the thermochromic materials can be used as such or in microencapsulated form. Advantageously, a master batch or coloured granules are first produced from the thermochromic material or the microencapsulated thermochromic material, which is then added to the plastic to be dyed.

In another advantageous embodiment of an aspect of the invention, the wall comprises at least one carrier material, preferably a polyamide material and/or a polybutylene terephthalate material, wherein the filter material and/or the thermochromic material is provided externally on the carrier material, internally on the carrier material and/or between at least two layers of the carrier material and/or is embedded in the carrier material.

Although in the context of the present invention, polyamide (PA) or polybutylene terephthalate (PBT) is preferably used as a carrier material or generally as the material of the wall, other plastics are also suitable for the device according to the invention, including the standard thermoplastics polyethylene (PE), polypropylene (PP), polystyrene (PS), polyvinyl chloride (PCV) and acrylonitrile-butadiene-styrene copolymer (ABS). Further suitable are the technical thermoplastics polycarbonate (PC), styrene-acrylonitrile copolymer (SAN), polymethyl methacrylate (PMMA), polyamide (PA), polyoxymethylene (POM), polybutylene terephthalate (PBT), polypropylene terephthalate (PPT), polyethylene terephthalate (PET) and polyphthalamide (PPA). Also suitable are the high-performance thermoplastics polyether ketone (PEK), poly(ether ether ketone) (PEEK), poly(ether ketone ketone) (PEKK), poly(ether ether ether ketone) (PEEEK), poly(ether ether ketone ketone) (PEEKK), poly(ether ketone ether ketone ketone)

(PEKEKK) and polyaryl ether ketone (PAEK). Fibre-reinforced plastics can also be used.

In another advantageous embodiment of an aspect of the invention, the quotient of the transmittance of the area of the wall, in at least the second temperature range, to radiation of the second wavelength or the second wavelength range and the transmittance of the wall, in at least the first temperature range, to radiation at least of the first wavelength or the first wavelength range is greater than 5, preferably greater than 10, and particularly preferably greater than 50.

In another advantageous embodiment of an aspect of the invention, the wall comprises a transmission area that, at least in the second temperature range, is permeable to radiation of the second wavelength or the second wavelength range, wherein the wall further has a reflection area on the side opposite the transmission area that, at least in the second temperature range, is configured to reflect or backscatter into the cavity radiation passing through the cavity of the second wavelength or the second wavelength range with a reflectance of at least 50%.

If the radiation that has passed through the dental material, i.e. has not yet been absorbed, is again sent by the reflection area due to said reflection back through the dental material, this causes an overall increase in the thermal yield, and the efficacy of the heater with respect to infrared radiation is improved.

The reflection area can comprise, preferably in contact with the dental material, i.e. on the inner side of the wall (as a coating or embedded), another thermochromic material, the switching temperature of which is coordinated with the temperature to which the dental material is to be heated (e.g. the temperature at the lower limit or the upper limit of the second temperature range or within said range), wherein the other thermochromic material has a reflectance of at least 50% with respect to the radiation of the second wavelength or the second wavelength range. This other thermochromic material thus on the one hand fulfils the purpose of the reflection area and on the other allows visual detection of the temperature reached, which is indicated by the colour change. In particular if the other thermochromic material absorbs the infrared radiation to a minimal degree or not at all, this temperature arises from the temperature of the adjacent dental material in the cavity.

In another advantageous embodiment of an aspect of the invention, the first temperature range is a range of 15 to 25° C., and the second temperature range is a range of 25 to 75° C.

Independently of the temperature ranges given here as advantageous, it is not necessary for the first temperature range to be directly contiguous to the second temperature range, even when this is provided in preferred embodiments of the invention.

In another advantageous embodiment of an aspect of the invention, the device comprises in the cavity a radiation-curable dental material, wherein the dental material is to be cured with the radiation of the first wavelength or the first wavelength range, wherein the dental material in the first temperature range, in particular at a temperature of 20° C., has a viscosity of greater than 400 Pa·s, and wherein the dental material in the second temperature range, in particular at a temperature of 60° C., has a viscosity of less than 150 Pa·s.

Preferably, the dental material has a viscosity in the first temperature range, in particular at a temperature of 20° C., of greater than 800 Pa·s, and particularly preferably greater than 1.200 Pa·s.

The dental material preferably has, in the second temperature range, in particular at a temperature of 60° C., a viscosity of less than 120 Pa·s, and particularly preferably less than 90 Pa·s.

It is also preferable if the quotient of the viscosity of the dental material in the second temperature range (e.g. at 60° C.) and the viscosity of the dental material in the first temperature range (e.g. at 20° C.) is less than 0.125, and particularly preferably less than 0.1.

In another advantageous embodiment of an aspect of the invention, the device comprises in the cavity a radiation-curable dental material which is a single-component composite composition comprising (A) monomers, (B) fillers and (C) initiators.

The dental, light-curable, single-component composite composition, preferably for producing a dental filling material, underfilling material, luting material or fissure sealant, can for example comprise:
- (A) monomers in an amount of 6 to 35 wt % based on the composite composition, preferably 10 to 35 wt %, and particularly preferably 10 to 25 wt %,
- (B) fillers in an amount of 65 to 93 wt %, preferably 65 to 89 wt %, and particularly preferably 75 to 89 wt % based on the composite composition,
- (C) initiators in an amount of 0.001 to 3 wt %, based on the amount of the composite composition,
- (D) further additives in an amount of 0.001 to 5 wt % based on the amount of the composite composition.

In a particular variant, component (A) of the dental, light-curable, single-component composite composition comprises the mixture of at least (A-i) a first monomer substance and (A-ii) a second monomer substance, wherein the viscosity of the second monomer substance (A-ii) at 20° C. is greater than 100 Pa·s, the viscosity of the first monomer substance (A-i) at 20° C. is greater than 100 mPa·s, the viscosity of the second monomer substance (A-ii) at 20° C. is greater than that of the first monomer substance (A-i) and the weight ratio of the first monomer substance (A-i) to the second monomer substance (A-ii) is in the range of 2:1 to 1:10, wherein the second monomer substance (A-ii) preferably comprises at least 40 wt % of 2,2-bis[4-(2-hydroxy-3-methacryloyloxypropoxy)phenyl]propane (bis-GMA) and/or light-curable derivatives of diisocyanate diphenylmethane (MDI) and/or light-curable derivatives of tetramethyl-m-xylylene diisocyanate (TMXDI), wherein the amount in wt % is based on the total weight of the monomer (A).

The investigations conducted by the inventors within the context of the present invention show that when components (A) to (D) are used in the indicated amounts (preferably in the content ranges given as preferable), specified viscosity values can be set in a particularly efficient manner.

Here:
- (A1) corresponds to the light-curable bi- or tricyclic compounds $Q(Y_xZ_e)_b$,
- (A2) corresponds to bis-GMA (2,2-bis[4-(2-hydroxy-3-methacryloyloxypropoxy)phenyl]propane) and/or the light-curable derivatives of MDI (diisocyanate diphenylmethane) and/or the light-curable derivatives of TMXDI,
- (A3) corresponds to the light-curable monomers, which are substances comprising one, two or more ethylenic groups, such as, for example, without this being limitative, the (meth)acrylate monomers that are commonly used in dental chemistry and are not to be classified as (A1) and (A2), (A4) corresponds to the light-curable bi- or tricyclic compounds $Q(Y_xZ_e)_b$, UDMA (7,7,9-trimethyl-3,14-dioxa-4,13-dioxo-5,12-diazahexadecane-1,16-dioxydi(meth)acrylate), BisEMA (alkoxylated bisphenol-A-di(meth)acrylate, where n=2-6), the hydroxyl-group-containing poly(meth)acrylates, the alkoxylated hydroxyl-group-containing poly(meth)acrylates and the light-curable chain-shaped and/or ring-shaped and/or cage-shaped polysiloxanes, (A5) corresponds to the light-curable monomers (A3) other than (A4).

In a preferred embodiment, the monomers (A) are composed of (A1) 10 to 60 wt %, preferably 20 to 50 wt %, and particularly preferably 25 to 40 wt % of light-curable bi- or tricyclic compounds $Q(Y_xZ_e)_b$, wherein Q denotes a saturated or olefinically unsaturated bi- or tricyclic structural element, each index b is a natural number selected from the group of the natural numbers 1, 2, and 3, each Z denotes a light-curable group, each index e is a natural number selected from the group of the natural numbers 1, 2 and 3, each Y denotes, in the structure $Q(Y_xZ_e)_b$, where x=1, a structural element that binds the structural element Q with e structural elements Z and denotes a linear or branched alkylene group, wherein the alkylene group can be interrupted by oxygen atoms and each index x is 0 or 1, (A2) 40 to 90 wt %, preferably 50 to 80 wt %, and particularly preferably 60 to 75 wt % of 2,2-bis[4-(2-hydroxy-3-methacryloyloxypropoxy)phenyl]propane (bis-GMA) and/or light-curable derivatives of diisocyanate diphenylmethane (MDI) and/or light-curable derivatives of tetramethyl-m-xylylene diisocyanate (TMXDI), (A3) 0 to 15 wt %, preferably 0 to 10 wt %, and particularly preferably 0 to 5 wt % further radically polymerizable monomers that are not to be classified as (A1) or (A2), wherein the amount in wt % of (A1), (A2) and (A3) are based on the total weight of the (A) monomers.

The dental, light-curable, single-component composite composition can further comprise e.g. (A) monomers, (B) fillers and (C) initiators, wherein the monomers (A) are composed of (A1) 10 to 60 wt %, preferably 20 to 50 wt %, and particularly preferably 25 to 40 wt % of light-curable bi- or tricyclic compounds $Q(Y_xZ_e)_b$, wherein Q denotes a saturated or olefinically unsaturated bi- or tricyclic structural element, each index b is a natural number selected from the group of the natural numbers 1, 2, and 3, each Z denotes a light-curable group, each index e is a natural number selected from the group of the natural numbers 1, 2 and 3, each Y denotes, in the structure $Q(Y_xZ_e)_b$, where x=1, a structural element that binds the structural element Q with e structural elements Z and denotes a linear or branched alkylene group, wherein the alkylene group can be interrupted by oxygen atoms and each index x is 0 or 1, (A2) 40 to 90 wt %, preferably 50 to 80 wt %, and particularly preferably 60 to 75 wt % of 2,2-bis[4-(2-hydroxy-3-methacryloyloxypropoxy)phenyl]propane (bis-GMA) and/or light-curable derivatives of diisocyanate diphenylmethane (MDI) and/or light-curable derivatives of tetramethyl-m-xylylene diisocyanate (TMXDI), (A3) 0 to 15 wt %, preferably 0 to 10 wt %, particularly preferably 0 to 5 wt %, and most particularly preferably 0 wt % of further radically polymerizable monomers that are not to be classified as (A1) or (A2), wherein the amounts in wt % of (A1), (A2) and (A3) are based on the total weight of the (A) monomers.

In a preferred variant of the two above embodiments, the dental material comprises an absorber component which, at least in the second temperature range, has an absorbance with respect to radiation of the second wavelength or the second wavelength range of more than 50%.

If the dental material is provided with an absorber component that is processed into, embedded into, or contained in the dental material, this absorbent material acts in a certain sense as a local heater in the dental material. Even if a known dental material per se already shows a certain degree of absorption of radiation of the second wavelength or the second wavelength range, this can be improved by the absorber component, wherein the separate absorber component additionally allows an extra degree of freedom in material selection of the actual dental material in that in this material selection one need not consider, or need consider only to a lesser degree, the absorption properties with respect to the radiation of the second wavelength or the second wavelength range.

The absorber component should ideally show no or only minimal absorption in the visible region, as there may otherwise occur an undesired colouration of the dental material or it may only be possible to use the absorber component to a limited extent.

An example of such an absorber component comprises a heat-absorbing glass with a content of iron oxide of 0.2% (preferably in the range of 2% to 4%) or more (calculated as FeO), wherein in this glass, compared to a silicate glass, which in addition to univalent, bivalent, and trivalent glass-forming oxides contains at least 25% silica ($SiO_2$), the silica content is completely or partially replaced by phosphoric acid ($P_2O_5$) and/or boric acid ($B_2O_3$), wherein the content of $P_2O_5$ or $B_2O_3$ or $P_2O_5$ and $B_2O_3$ is at least 25%. If, by means of suitable measures (e.g. reduced melting, reducing additives; in particular, addition of phosphorus compounds of low oxidation stages down to phosphides (including phosphorus) (e.g. calcium hypophosphite ($Ca[H_2PO_2]_2$); iron phosphide ($Fe_3P$)) during melting and cooling in order to achieve extensive reduction) dissolution of the iron dye as iron oxydul is achieved, one thus obtains an iron oxydul phosphate glass, an iron oxydul borate glass or an iron oxydul phosphate borate glass. In order to decrease water solubility, it can be provided that the glass comprises 10% or more of alumina ($Al_2O_3$) or aluminium compounds corresponding to 10% or more of alumina. Preferably, the glass comprises less silica than phosphoric acid, boric acid or the combination of phosphoric acid and boric acid.

As an absorber component, for example, one can also use a heat-absorbing optical filter material such as that available under the brand name Schott KG5, wherein the filter materials KG4 to KG1 can also be used to a lesser extent.

Although the above are examples of a material for the absorber component that is inorganic, the invention is not limited in this respect, and it also possible to use an organic absorber component, wherein a combination of inorganic and organic materials is also possible.

In another advantageous embodiment of an aspect of the invention, the device has in the cavity an absorption area comprising or consisting of an absorbent material which, at least in the second temperature range, has an absorbance with respect to radiation of the second wavelength or the second wavelength range of more than 50%.

Alternatively or additionally to the absorption by the dental material, the device itself can also be equipped with an "internal heating element" in the form of the absorption area arranged in the cavity, wherein this absorption area can optionally be equipped with an enlarged surface (e.g. in the form of ribs) in order in this manner to allow particularly favourable heat transfer to the dental material.

In another advantageous embodiment of an aspect of the invention, the device is selected from the group composed of syringes, application needles and compules.

In another advantageous embodiment of an aspect of the invention, the device comprises an application tip for applying the dental material, wherein the application tip has an outlet opening for the dental material, wherein the outlet opening preferably has an outlet cross-sectional area in the range of 0.2 to 3.0 mm², preferably not more than 2.0 mm², and particularly preferably not more than 1.5 mm².

In the first temperature range, the sufficiently high viscosity allows drop-free storage and holding, so that for example contamination of working surfaces can be prevented. On the other hand, the heating (e.g. to 40° C. to 80° C.) results in selectively reduced viscosity, which makes it possible to equip the device with an application tip with a relatively small outlet cross-sectional area in order to ensure pinpoint application in treatment.

In an advantageous embodiment of an aspect of the invention, the wall of the provided device, before irradiation with the radiation of the second wavelength or the second wavelength range and during irradiation with the radiation of the second wavelength or the second wavelength range, blocks and/or reflects radiation of the first wavelength or the first wavelength range and allows radiation of the second wavelength or the second wavelength range to pass through to the dental material.

In another advantageous embodiment of an aspect of the invention, dispensing of the dental material from the device is provided as a further step.

In a preferred variant of the above embodiment, irradiation of the dental material with radiation of the first wavelength or the first wavelength range is provided as a further step so that the dental material is cured.

In another advantageous embodiment of an aspect of the invention in the form of a dental therapeutic method, dispensing of the dental material from the device is provided as a further step, wherein the dental material, while or after being dispensed from the device, is placed in the oral cavity of a patient and preferably allowed to cool there and/or is subsequently irradiated with radiation of the first wavelength or the first wavelength range in such a way that it is cured.

In another advantageous embodiment of an aspect of the invention in the form of a dental therapeutic method, the dental material is brought into contact with a tooth of a patient to be treated, preferably as a filling material, an underfilling material, a luting material or a fissure sealant.

According to a further aspect of the invention, use of a filter material is proposed for producing a device according to the invention comprising such a filter material.

According to a further aspect of the invention, use of a thermochromic material is proposed for producing a device according to the invention.

According to a further aspect of the invention, use of an absorbent material is proposed for producing a device according to the invention in which the absorbent material is incorporated as an absorber component into the radiation-curable dental material.

According to a further aspect of the invention, a dental system or a kit comprising a device according to the invention and a radiation source for the radiation of the second wavelength or the second wavelength range is proposed, wherein the dental system or the kit can further comprise a radiation source for the radiation of the first wavelength or the first wavelength range.

Features of advantageous embodiments of the invention are defined in particular in the dependent claims, wherein further advantageous features, embodiments and configurations are also to be derived by the person having ordinary skill in the art from the above explanation and the following discussion.

Figure 2:
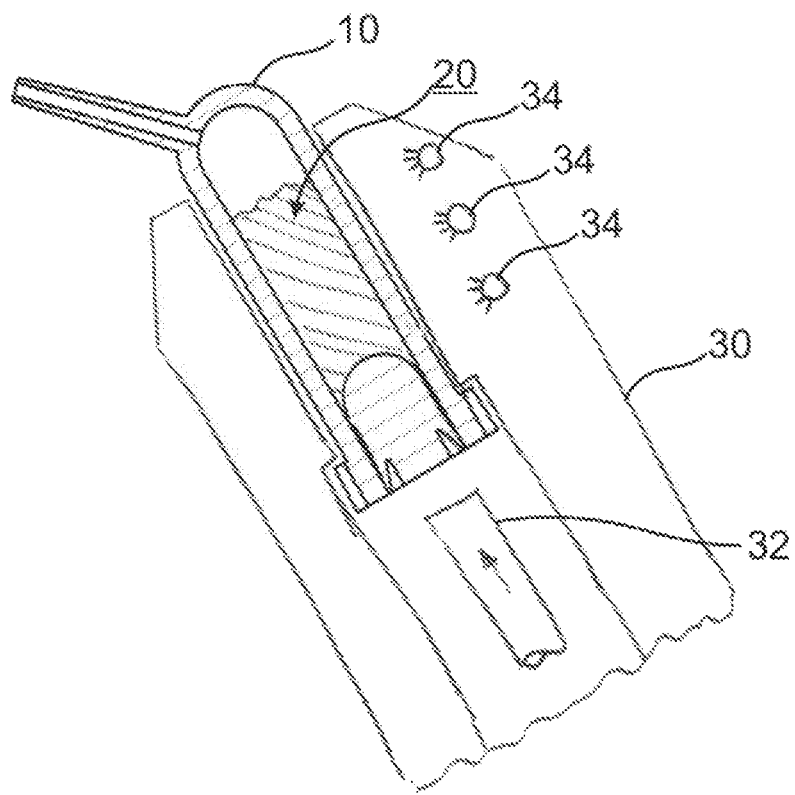
Figure 3:
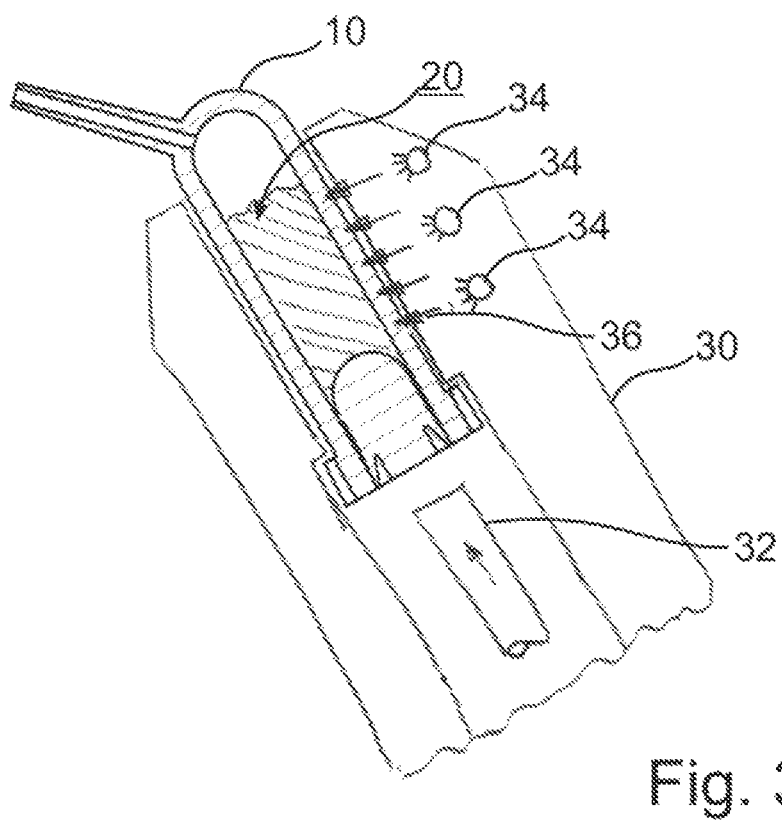
Figure 4:
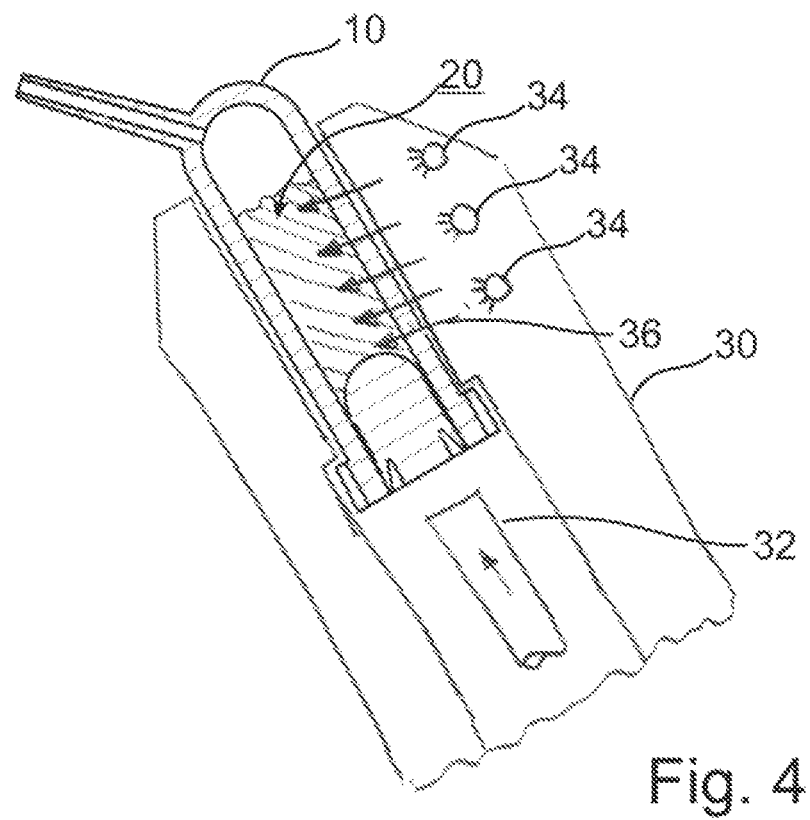
Figure 5:
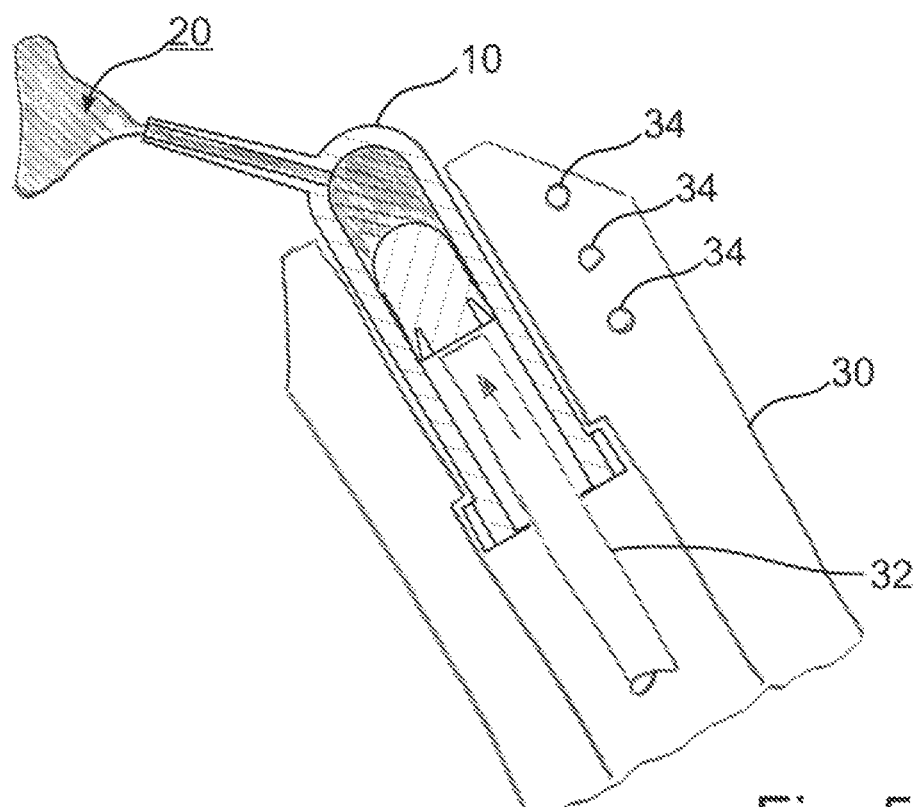
Figure 6:
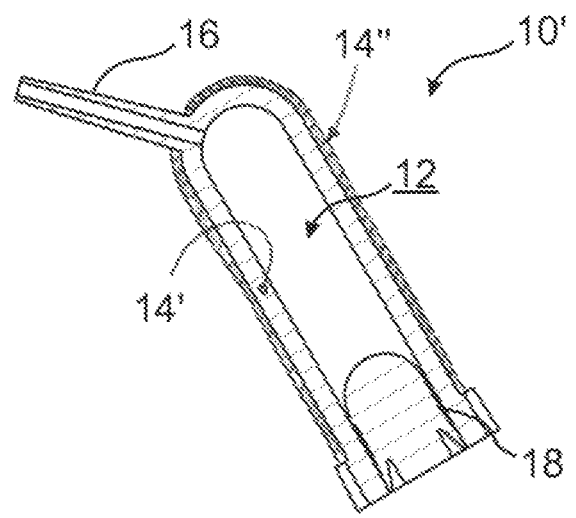
Figures 7, 8:
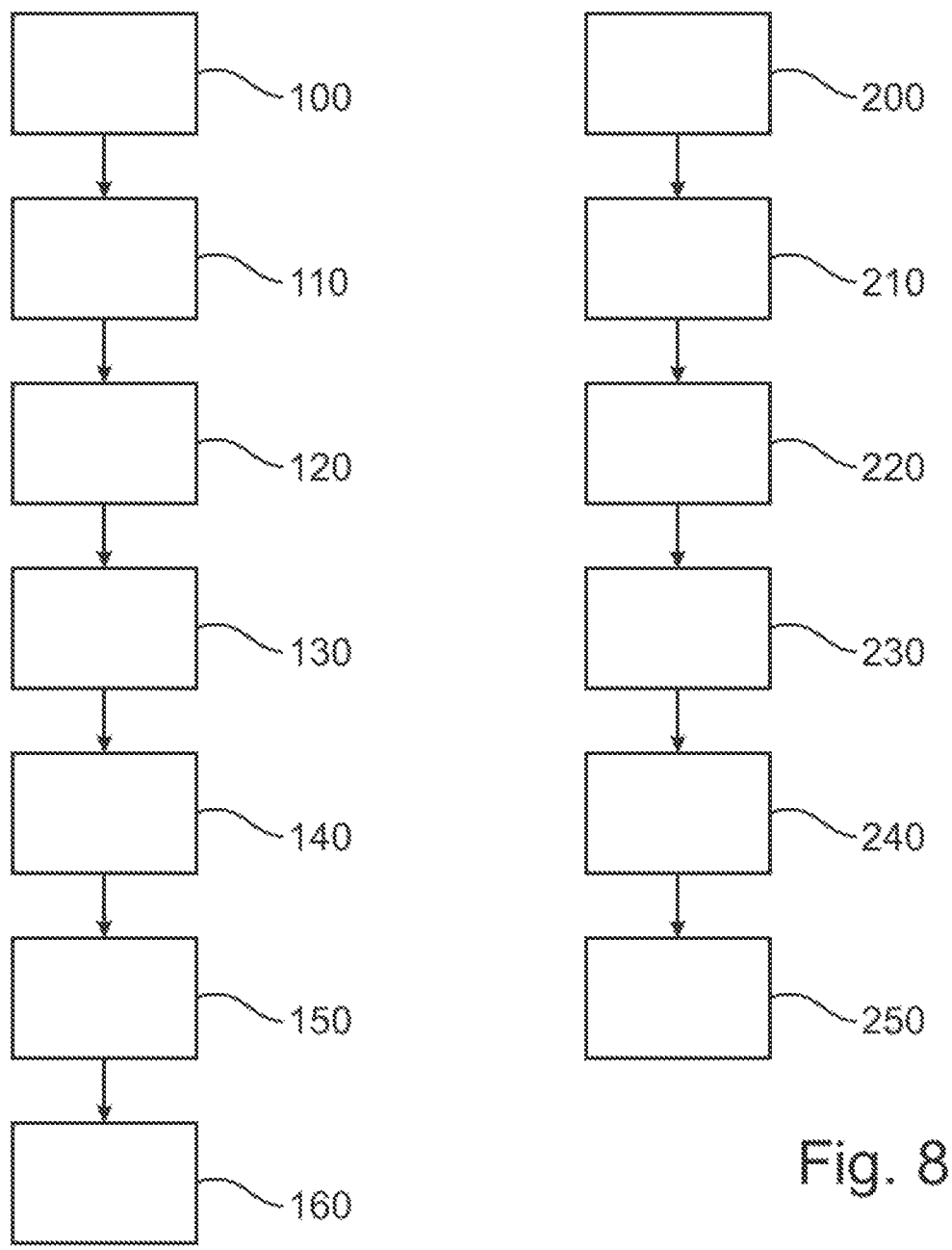

In the following, the present invention is further illustrated and explained with reference to the examples shown in the figures. The figures show the following:

FIG. 1 a schematic view illustrating a first example of the device according to the invention, FIG. 2 a further schematic view illustrating a first example of the device according to the invention and its use, FIG. 3 a further schematic view illustrating a first example of the device according to the invention and its use, FIG. 4 a further schematic view illustrating a first example of the device according to the invention and its use, FIG. 5 a further schematic view illustrating a first example of the device according to the invention and its use, FIG. 6 a schematic view illustrating a second example of the device according to the invention, FIG. 7 a schematic flow chart of a first example of the method according to the invention for treating a dental material and FIG. 8 a schematic flow chart of a second example of the method according to the invention for treating a dental material.

In the attached drawings and the explanations of these drawings, elements that correspond or relate to one another are identified—where appropriate—with respectively corresponding or similar reference numbers, even when they are to be found in different examples.

FIG. 1 shows a schematic view illustrating a first example of the device according to the invention.

In the first example, the device 10 is configured as a compule that has a cavity 12 designed for storage dental material (not shown in FIG. 1). The cavity 12 is surrounded by a wall 14 of the compule 10, which is in turn provided with an application tip 16. The available part of the cavity 12 is additionally delimited by a piston 18 that is arranged inside the wall 14 of the compule 10 so as to be movable along a longitudinal axis of the compule 10 in order to allow dental material located in the cavity 12 to be dispensed via the application tip 16.

As the compules as such, the structure and the use thereof are known, a further explanation thereof can be avoided with here.

However, it should be noted that the description of the invention based on examples in the form of a compule is not to be understood as a limitation, as the invention generally provides a device suitable for storage and application that can be implemented not only by means of a compule, but for example by means of a syringe or an application needle.

FIG. 2 shows a further schematic view illustrating a first example of the device according to the invention and its use.

The compule 10 shown in FIG. 1 is shown here with the dental material 20 stored in the cavity 12, wherein the piston 18 is additionally in an initial position, i.e. at the maximum distance from the application tip 16, so that the part of the cavity 12 available for the dental material 20 is maximized. In the view of FIG. 2, an area of the cavity 12 adjacent to the application tip 16 is not filled with dental material 20, wherein, however, complete filling of the cavity can also be provided. In the first temperature range (e.g. at 20° C.), the dental material preferably has such high viscosity that the application tip 16 provides resistance that is too high to allow dispensing.

The compule 10 is accommodated in an application tip of compule applicator 30, wherein the compule applicator 30 comprise, in a known manner, a ram 32 for advancing the piston 18 in the compule 10 that is otherwise held by the compule applicator 30. The compule applicator 30 are additionally equipped in the area of the held compule 10 with a plurality of radiation sources in the form of infrared LEDs 34.

FIG. 3 shows a further schematic view illustrating a first example of the device according to the invention and its use.

The view of FIG. 3 corresponds to that of FIG. 2, wherein in FIG. 3, however, a situation is illustrated in which, by means of the IR LEDs 34 of the compule applicator 30, radiation 36 in the infrared region (in particular in the near infrared region) is irradiated onto the compule 10.

In the present example, the wall 14 of the compule 10 comprises a thermochromic material, which e.g. at 20° C. is impermeable to the incident infrared radiation. In addition, the wall 14 is impermeable to radiation of the wavelength or wavelengths that can be used for light curing of the dental material 20. This is significant in that this provides protection of the dental material 20 contained therein that is integrated with the compule 10 itself, so that the compule 10 can be handled without worry about the possibility that undesired light irradiation into the interior will trigger curing of the dental material 20.

The infrared radiation from the IR LEDs 34 into the wall 14 heats the wall 14, provided that the radiation there is at least partly absorbed. In this case, it should be clear that the energy input from the IR LEDs 34 must be sufficient to exceed any losses due to heat conduction, radiation, etc.

A preferred combination of the aspects discussed in the present application lies in particular in a device (e.g. in the form of a compule) composed of polyamide with the above-mentioned perylene derivatives (5) and (6) as a filter material and a radiation in the near infrared region for heating (in particular with a wavelength of 800 to 1000 nm), wherein in this case the monomers (A) of the dental material composed of the material specified in (A1) to (A3) are preferably present.

FIG. 4 shows a further schematic view illustrating a first example of the device according to the invention and its use.

The view of FIG. 4, as is the case for that of FIG. 3, corresponds to the view of FIG. 2, wherein in FIG. 4, however, a situation is illustrated in which by means of the IR LEDs 34 of the compule applicator 30, so much radiation 36 in the infrared region (in particular in the near infrared region) has been irradiated onto the compule 10 (as shown in FIG. 3) that the thermochromic material has been heated above its switching temperature and has thus become (more) permeable to the infrared radiation.

As shown in FIG. 4, the infrared radiation now reaches directly into the dental material 20, which can thus be heated.

It is not necessary for the complete wall 14 to have or take on permeability to the infrared radiation, provided that a sufficiently large area of the wall (that does not necessarily have to be continuous) has the necessary permeability.

Similarly, it is not necessarily the case that the entire thermochromic material present in the wall 14 or the area of the wall 14 be heated above the switching temperature, provided that a desired sufficient heat input in the dental material 20 is ensured.

It can additionally be provided (not shown) that the compule 10 on or in the wall 14 on the side opposite the IR LEDs 34 has a reflection area for the radiation 36 used, which is thus reflected back into the dental material 20.

By enabling corresponding visibility (e.g. by means of an opening or a recess in the compule applicator 30), the wall 14 can also advantageously be provided with a further thermochromic material, the switching temperature of which is coordinated with the desired temperature of the dental material 20 so that the colour change indicates that the desired temperature has been reached. If the further thermochromic material has reflection properties for the infrared radiation used, it can also be used for the above-mentioned reflection area.

FIG. 5 shows a further schematic view illustrating a first example of the device according to the invention and its use.

FIG. 5 continues from the view of FIG. 4. After the dental material 20 contained in the compule 10 has been sufficiently heated through the wall 14 using the IR LEDs 34, i.e. after a desired reduced viscosity has been achieved, the ram 32 is pressed forward over the piston 18 in order to dispense the dental material 20 through the application tip 16 of the compule 10.

FIG. 6 shows a schematic view illustrating a second example of the device according to the invention.

In the second example as well, the device 10' is configured as a compule comprising a cavity 12 that is designed for the storage of dental material (not shown in FIG. 6). The cavity 12 is surrounded by a wall of the compule 10', which in turn is equipped with an application tip 16. The available part of the cavity 12 is additionally delimited by a piston 18 that is arranged inside the wall 14' of the compule 10', such that it is moveable along a longitudinal axis of the compule 10', so that the dental material located in the cavity 12 can be dispensed through the application tip 16.

In contrast to the first example, which is illustrated in FIGS. 1 to 5 and in which the thermochromic material in the material itself is contained in a substantially homogeneous (or at least single-layer) wall 14 of the compule 10, in the second example, the wall has a layered configuration, wherein in the example shown in FIG. 6, a conventional compule with a wall layer 14' is provided with an additional outer layer 14" that comprises the thermochromic material.

Together with the wall layer 14', the outer layer 14" forms the wall of the compule 10' and can for example be configured in the form of a film that covers the wall layer 14', a lacquer, a label, or a shrink tube.

Installation on the inside of the wall layer is also conceivable, wherein a coating of three or more layers is also possible.

In each of the two examples discussed above, thermochromic material is provided in or on the wall or wall layer. With the exception of FIG. 3, the above embodiments also apply in a correspondingly adapted manner in cases where a filter material is provided. It is also possible to provide a combination of a filter material and a thermochromic material.

FIG. 7 shows a schematic flow chart of a first example of the method according to the invention for treating a dental material.

In step 100, a device according to the invention with radiation-curable dental material stored therein is first provided, wherein the dental material and the device each have a temperature of 20° C.

Because of the impermeability to blue light, for example, which is provided for the curing of dental material, the provided device protects the dental material from undesired initiation of the curing process.

In step 110, the device is irradiated with infrared radiation in the range of 750 nm to 3,000 nm, wherein the infrared radiation is first absorbed by the wall of the device or the thermochromic material contained therein, and is thus heated.

In step 120, the switching temperature of the thermochromic material is reached, which causes the thermochromic material to become permeable to the infrared radiation, so that in step 130 the dental material in the device is reached by the infrared radiation and thus heated.

By the heating of the dental material in step 140, the viscosity of the dental material is reduced to a desired viscosity or less, which e.g. can be reached at a temperature of 50° C.

In step 150, the dental material, which has the desired viscosity or even a lower viscosity, is dispensed from the device.

In step 160, the dispensed dental material is irradiated with blue light in order to initiate and carry out the curing process.

FIG. 8 shows a schematic flow chart of a second example of the method according to the invention for treating a dental material.

In step 200, a device according to the invention with radiation-curable dental material stored therein is first provided, wherein the dental material and the device each have a temperature of 20° C.

Because of the impermeability to blue light, for example, which is provided for the curing of dental material, the provided device protects the dental material from undesired initiation of the curing process.

In step 210, the device is irradiated with infrared radiation in the range of 750 nm to 3,000 nm.

On provision of the device in step 200 and also during irradiation with infrared radiation, the wall blocks and/or reflects, with its filter material, radiation of the first wavelength or the first wavelength range (e.g. blue light), but allows the infrared radiation—unlike in the case of FIG. 7—to pass through to the dental material.

As the wall is permeable to the infrared radiation, in step 220, the dental material is reached in the device by the infrared radiation and thus heated.

With the heating of the dental material, in step 230, the viscosity of the dental material is decreased to a desired viscosity or less, which e.g. can be reached at a temperature of 50° C.

In step 240, the dental material, which has the desired viscosity or even a lower viscosity, is removed from the device.

In step 250, the dispensed dental material is irradiated with blue light in order to initiate and carry out the curing process.

The respective steps illustrated in FIGS. 7 and 8 take place outside the human or animal body and as such have no therapeutic action or any interaction with a human or animal body. In the context of the present invention, however, a therapeutic use can also be provided, in which e.g. curing of the dental material takes place in or on the tooth or in the oral cavity.

Although various aspects or features of the invention are shown respectively in the figures in combinations, it is obvious to the person having ordinary skill in the art—unless otherwise indicated—that the combinations shown and discussed are not the only ones possible. In particular, units or complexes of features corresponding to one another from different examples can be interchanged with one another.

LIST OF REFERENCE NUMBERS 10, 10' Compule
12 Cavity
14 Wall
14' Wall layer
14" Outer layer
16 Application tip
18 Piston
20 Dental material
30 Compule applicator
32 Ram
34 IR LED
36 Radiation
100, 200 Step of providing the device
110, 210 Step of irradiating the provided device
120 Step of reaching the thermochromic material
130, 220 Step of heating the dental material
140, 230 Step of reducing the viscosity of the dental material
150, 240 Step of dispensing the dental material from the device
160, 250 Step of irradiating the dental material

The invention claimed is:

1. A device (10, 10') for storage and application (20), comprising
a cavity (12) for storage of a dental material (20) and
a wall (14) surrounding the cavity (12),
wherein the wall (14), in at least a first temperature range, is impermeable to radiation of at least a first wavelength or a first wavelength range in the range of 100 nm to 500 nm, and
wherein the wall (14)
has at least one area with a carrier material and a filter material which is provided externally on the carrier material, internally on the carrier material and/or between at least two layers of the carrier material and/or is embedded in the carrier material, wherein the filter material is selected from the group composed of: perylene derivatives

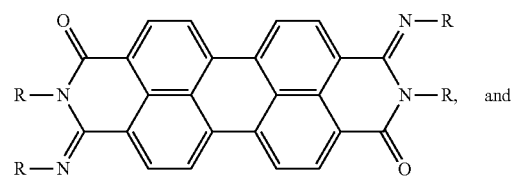

(3)

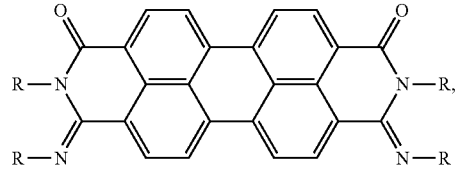

(4)

and combinations thereof,
wherein two N—R groups that are separated by one carbon atom join together to form imidazoles, annulated imidazoles, pyrimidones, or annulated pyrimidones.

2. The device (10, 10') according to claim 1,
wherein the area of the wall (14) comprises or is composed of the filter material,
wherein the filter material, at least in the first temperature range, has a transmittance with respect to radiation of the first wavelength or the first wavelength range of less than 10%,
wherein the filter material, at least in a second temperature range, has a transmittance with respect to radiation of a second wavelength or a second wavelength range in a range of 600 nm to 50,000 nm of more than 50%.

3. The device (10, 10') according to claim 2,
wherein the filter material comprises aromatic diazo compounds.

4. The device (10, 10') according to claim 1,
wherein the area of the wall (14) comprises or is composed of thermochromic material having a switching temperature in the range of 25 to 50° C.,
wherein the thermochromic material, at a temperature below the switching temperature, has lower transmittance with respect to radiation at least of a second wavelength or a second wavelength range in a range of 600 nm to 50,000 nm than at a temperature above the switching temperature.

5. The device (10, 10') according to claim 4,
wherein the thermochromic material is selected from the group composed of inorganic pigments comprising metal salts or metal oxides in which a colour transition takes place due to a phase transmission, a change in a ligand geometry, a change in a coordination number and/or a change in a crystal field, organic pigments comprising thermochromic liquid crystals, conjugated polymers and leuco dyes and combinations thereof.

6. The device (10, 10') according to claim 4,
wherein the thermochromic material (14") is provided externally on the carrier material (14'), internally on the carrier material and/or between at least two layers of the carrier material and/or is embedded in the carrier material.

7. The device (10, 10') according to claim 1,
wherein a quotient of the transmittance of the area of the wall (14), at least in a second temperature range, with respect to radiation of a second wavelength or a second wavelength range in a range of 600 nm to 50,000 nm and the transmittance of the wall (14) in at least the first temperature range with respect to radiation at least of the first wavelength or the first wavelength range is greater than 5.

8. The device (10, 10') according to claim 1,
wherein the wall (14) has a transmission area which, at least in a second temperature range, is permeable to radiation of a second wavelength or a second wavelength range in a range of 600 nm to 50,000 nm,
wherein the wall (14) further has a reflection area on a side opposite the transmission area that is configured, at least in the second temperature range, to reflect or backscatter radiation of the second wavelength or the second wavelength range passing through the cavity (12) with a reflectance of at least 50% into the cavity (12).

9. The device (10, 10') according to claim 1,
wherein the first temperature range is a range of 15 to 25° C.

10. The device (10, 10') according to claim 1, comprising in the cavity (12) the dental material (20),
wherein the dental material (20) is to be cured with the radiation of the first wavelength or the first wavelength range,
wherein the dental material (20) in the first temperature range, in particular at a temperature of 20° C., has a viscosity of greater than 400 Pa's and
wherein the dental material (20) in a second temperature range, in particular at a temperature of 60° C., has a viscosity of less than 150 Pa·s.

11. The device (10, 10') according to claim 10,
wherein the dental material (20) comprises an absorber component which, at least in a second temperature range, has an absorbance with respect to radiation of a second wavelength or second wavelength range in a range of 600 nm to 50,000 nm of more than 50%.

12. The device (10, 10') according to claim 1, comprising in the cavity (12) the dental material (20), which is a single-component composite composition comprising
(A) monomers,
(B) fillers and
(C) initiators.

13. The device (10, 10') according to claim 1, wherein the device (10, 10') comprises an absorption area in the cavity (12) comprising or consisting of an absorbent material which, at least in the second temperature range, has an absorbance with respect to radiation of the second wavelength or the second wavelength range of more than 50%.

14. The device (10, 10') according to claim 1, selected from the group composed of syringes, application needles and compules.

15. The device (10, 10') according to claim 1, comprising:
an application tip (16) for applying the dental material (20), wherein the application tip (16) comprises an outlet opening for the dental material (20),
wherein the outlet opening has an outlet cross-sectional area in the range of 0.2 to 3.0 mm².

16. A device (10, 10') for storage and application (20) comprising
a cavity (12) for storage of a dental material (20) and
a wall (14) surrounding the cavity (12),
wherein the wall (14), in at least a first temperature range, is impermeable to radiation of at least a first wavelength or a first wavelength range in the range of 100 nm to 500 nm and
wherein the wall (14) has at least one area with a carrier material and a filter material which is provided externally on the carrier material, internally on the carrier material and/or between at least two layers of the carrier material and/or is embedded in the carrier material, wherein the filter material is selected from the group composed of:
perylene derivatives

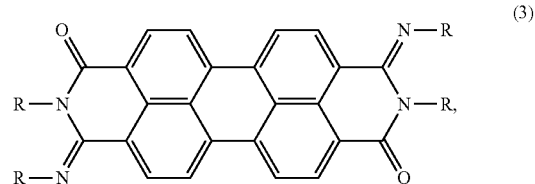

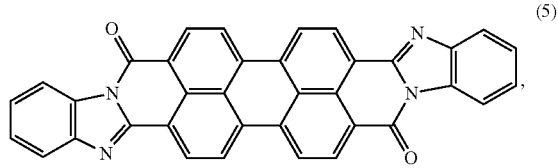

-continued
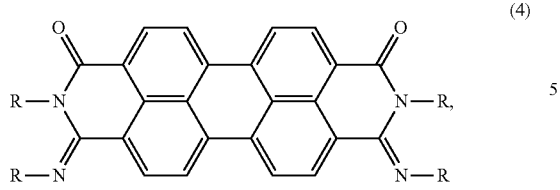
(4)
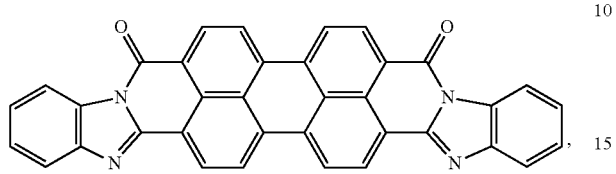
(6)
and combinations thereof,
wherein in perylene derivatives (3) and (4), two N—R groups that are separated by one carbon atom join together to form imidazoles, annulated imidazoles, pyrimidones, or annulated pyrimidones.
* * * * *